United States Patent
Fukasawa et al.

US007256031B2

(10) Patent No.: US 7,256,031 B2
(45) Date of Patent: Aug. 14, 2007

(54) ENZYME HAVING β-GLUCOSIDASE ACTIVITY AND USE THEREOF

(75) Inventors: Tomoyuki Fukasawa, Saitama (JP); Chuhei Nojiri, Saitama (JP); Nobuo Matsuhashi, Saitama (JP); Koji Nishizawa, Saitama (JP); Kaoru Okakura, Kanagawa (JP); Takashi Yamanobe, Ibaraki (JP)

(73) Assignees: Meiji Seika Kaisha, Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 436 days.

(21) Appl. No.: 10/381,434

(22) PCT Filed: Sep. 28, 2001

(86) PCT No.: PCT/JP01/08536

§ 371 (c)(1),
(2), (4) Date: Mar. 31, 2003

(87) PCT Pub. No.: WO02/26979

PCT Pub. Date: Apr. 4, 2002

(65) Prior Publication Data

US 2004/0091469 A1    May 13, 2004

(30) Foreign Application Priority Data

Sep. 29, 2000    (JP) ............................. 2000-298262

(51) Int. Cl.
| | | |
|---|---|---|
| C07H 21/04 | (2006.01) | |
| C12N 9/42 | (2006.01) | |
| C12N 1/12 | (2006.01) | |
| C12N 15/00 | (2006.01) | |
| C12P 21/06 | (2006.01) | |

(52) U.S. Cl. .................. 435/209; 435/4; 435/6; 435/69.1; 435/183; 435/41; 435/252.3; 435/320.1; 536/23.2; 536/23.4; 536/23.5; 536/23.7; 426/56; 426/549

(58) Field of Classification Search .................... 435/4, 435/6, 69.1, 183, 190, 200, 201–210, 252.3, 435/320.1; 536/23.2, 23.7, 23.74
See application file for complete search history.

(56) References Cited

U.S. PATENT DOCUMENTS 4,562,150 A * 12/1985 Yamanobe et al. ........... 435/99

FOREIGN PATENT DOCUMENTS

| JP | 59-166081 | 9/1984 |
|---|---|---|
| JP | 4-117244 | 4/1992 |
| JP | 7-236431 | 9/1995 |
| JP | 7-264994 | 10/1995 |
| WO | 92/10581 | 6/1992 |

OTHER PUBLICATIONS

Takashi Kawaguchi et al.: "Cloning and sequenceing of the cDNA encoding beta-glucosidase 1 from *aspergillus aculeatus* " GENE, vol. 173, No. 2, pp. 287-288, 1996.
SM Pitson et al.: "Purification and characterization of an extracellular beta-glucosidase from the filamentous fungus acremonium persicinum and its probable role in beta-gluccan degradation" Enzyme Microb Technol., vol. 21, No. 3, pp. 182-190, Aug. 15, 1997.
Supannee Kansarn et al.: "Purification and characterization of three beta-glucosidases from *acremonium cellulolyticus*" Shizuoka Daigaku Daigakuin Denshi Kagaku Kenkyuu-Ka Kenkyuu Houkoku, No. 21, pp. 9-15 Mar. 31, 2000.

* cited by examiner

*Primary Examiner*—Manjunath Rao
(74) *Attorney, Agent, or Firm*—Oblon, Spivak, McClelland, Maier & Neustadt, P.C.

(57) ABSTRACT

The invention is to provide a novel β-glucosidase and a gene that codes for the enzyme, and to develop a technique of utilizing the β-glucosidase or a composition that contains the enzyme for processing plants or plant-derived substances.

According to the invention, there are provided a novel enzyme showing a β-glucosidase activity and derived from filamentous fungi of the genus Acremonium, a gene that codes for the enzyme, a method of using the gene for expressing β-glucosidase, an enzyme composition that contains β-glucosidase, and a method of processing plants or plant-derived substances with the enzyme or the enzyme compositions.

65 Claims, 3 Drawing Sheets

ENZYME HAVING β-GLUCOSIDASE ACTIVITY AND USE THEREOF

DESCRIPTION

1. Technical Field

The present invention relates to a novel enzyme having β-glucosidase activity and its use, precisely to such a novel enzyme with β-glucosidase activity that is derived from microorganisms belonging to the genus *Acremonium*, to a composition comprising the enzyme and to their use.

2. Background Art

Cellulose is an essential constitutive component of cells of higher plants and widely exists in nature. Cellulose is a polysaccharide polymer of glucose polymer of glucose molecules polymerized through β-1,4-glucoside linkage. In nature, crystalline or amorphous cellulose exists, and bonding in a complicated manner to other components, lignin, hemicelluloses, pectins and the like, it constructs plant tissues.

Cellulose is a generic term for a group of enzymes that catalyze the reaction of degrading cellulose into cello-oligosaccharides, cellobiose and finally into glucose. Depending on its reaction mode, it may be grouped into endoglucanase, exoglucanase, β-glucosidase, etc. When their reaction modes are compared with each other in detail, it is believed that multiple enzymes that act in different reaction modes compensate for each other to exhibit some synergistic effects, thereby degrading cellulose which is the essential ingredient of plant cell walls.

It is believed that β-glucosidase catalyzes a reaction on cello-oligosaccharides, cellobiose or glycosides with aglycone linked thereto via β-D-glucopyranosyl linkage to thereby liberate glucose from them, and it is the important enzyme in the final stage of cellulose saccharification and in glucose liberation from glycosides.

Regarding the application of β-glucosidase to various fields, for example, in the field of feed, it is added to feed to thereby increase the body weight of farm animals and/or to improve the feed efficiency. Enzyme for silage is added to grass when it is put into silos so as to improve the quality of fermented silage to thereby obtain silage of good quality. For that purpose, various enzyme preparations are available on the market, for example, preparations that contain cellulase, hemicellulase or amylase alone, or compound preparations of such enzymes, and even other compound preparations of such enzymes with lactic acid bacteria that are for further enhancing the effect of the enzymes. However, enhancing the activity of β-glucosidase may improve the saccharification efficiency for cellulose with it, and may produce silage of better quality.

In the field of food, the enzyme may be utilized for increasing the aromatic compound in juice, wine, etc.; for increasing the clarity of juice, decreasing the viscosity thereof, improving the color thereof and removing the bitterness from it; and for increasing the fermentation efficiency in brewing and baking. In the field of medicine, the enzyme may be utilized for reagents for clinical checkups. In the other fields, the enzyme may be utilized for promoting saccharification of cellulose biomass into glucose and for improving the efficiency of treating wastes of cellulose products.

Regarding the enzyme produced by a type of filamentous fungi, *Acremonium cellulolyticus*, cellulase is characterized by the strong saccharification activity thereof, and its effectiveness in use in feed and silage has been reported (JP-A-4-117244 and 7-236431). In addition, the cellulose component contained therein has also been reported (Agric. Biol. Chem., 52, 2493-2501 (1988); ibid., 53, 3359-3360 (1989); ibid., 54, 309-317 (1990)).

In addition, it has been reported that the β-glucosidase activity among cellulase is extremely higher than that of any other known cellulase, for example, that from *Trichoderma resei* (JP-B-60-43954).

Further, β-glucosidase produced by *Acremonium cellulolyticus* was purified into three different types pure products (Report by the Electronic Science Postgraduate Course of the Shizuoka University, 21, 9-15 (2000)). These enzyme products were highly purified and analyzed in detail for their enzymatic and proteinaceous properties, but no one has reached amino acid sequencing of the enzyme and gene isolation from the enzyme.

For effective industrial utilization of β-glucosidase, it is indispensable to isolate and purify the enzyme and to clarify the enzymatic and physical properties thereof. In addition, for enabling increased expression of the enzyme and mass-production thereof, it is necessary to isolate and analyze the gene that codes for the enzyme.

The present invention is to provide a novel β-glucosidase protein, a gene that codes for the β-glucosidase, a method of using the gene for expressing the β-glucosidase, an enzyme composition that contains the β-glucosidase, and a method of treating plants and/or plant-derived substances with the β-glucosidase or the enzyme composition.

To solve the problems noted above, we, the present inventors have fractionated and purified various enzymes that construct cellulases of *Acremonium cellulolyticus*, and assiduously studied them. In the group of the enzymes, as a result, we have found a novel β-glucosidase that differs from any other known β-glucosidase and have isolated a gene that codes for the enzyme.

The enzyme shows an extremely higher relative activity than any of the above-mentioned, *Acremonium cellulolyticus*-derived three types of β-glucosidase.

In addition, we have further studied the action and the effect of the β-glucosidase on various plants or plant-derived substances, and have completed the present invention.

DISCLOSURE OF THE INVENTION

Specifically, the invention provides the following:

The present invention provides an enzyme showing a β-glucosidase activity, which is derived from microorganisms of the genus *Acremonium* and has the following characteristics:

(a) substrate specificity, action characteristics: the enzyme acts on the cello-oligosaccharides and on glycosides with aglycone linked thereto via β-D-glucopyranosyl linkage to produce glucose;

(b) molecular weight: 108,000 (through SDS-polyacrylamide gel electrophoresis);

(c) isoelectric point pI 4.7 (through polyacrylamide gel isoelectric focusing);

(d) optimum pH: it falls between pH 3.5 and 4.0;

(e) optimum temperature for action: it is 70° C.

In one embodiment of the enzyme described above, the microorganisms of the genus *Acremonium* are those of *Acremonium cellulolyticus*.

The present invention, also provides a β-glucosidase having the following characteristic (a), (b) or (c);

(a) a protein that contains a part of or the 1st to 838th sequence of the amino acid sequence of Sequence ID NO 2 of the Sequence Listing;

(b) the protein (a) which further contains a part or all of the —20th to —1st amino acid sequence of Sequence ID NO 2 of the Sequence Listing, at its N-terminal side;

(c) a modified protein which has the amino acid sequence of above (a) or (b) and has a β-glucosidase activity.

In one embodiment of the β-glucosidase described above, it is derived from filamentous fungi.

In one embodiment of the β-glucosidase described above, the filamentous fungi are microorganisms of the genus *Acremonium*.

In one embodiment of the β-glucosidase described above, the microorganisms of the genus *Acremonium*, are those belonging to *Acremonium cellulolyticus*.

The present invention also provides a gene comprising the following DNA (a), (b) or (c);

(a) a DNA comprising the base sequence of Sequence ID NO 1 of the Sequence Listing;

(b) a DNA including a modified sequence of the base sequence of above (a) and coding for a protein having a β-glucosidase activity;

(c) a DNA coding for a protein that comprises an amino acid sequence of Sequence ID No 2 of the Sequence Listing or for a modified protein thereof.

In one embodiment of the gene described above, it is derived from filamentous fungi.

In one embodiment of the gene described above, the filamentous fungi are microorganisms of the genus *Acremonium*.

In one embodiment of the gene described above, the microorganisms of the genus *Acremonium* are those belonging to *Acremonium cellulolyticus*.

The present invention also provides a DNA construct that comprises the DNA sequence described above or a modified sequence thereof.

The present invention also provides an expression vector that contains the DNA sequence described above.

The present invention also provides a host cell transformed with the DNA construct or the expression vector described above.

In one embodiment of the host cell described above, the host is any of coliform bacteria, yeast, actinomycetes or filamentous fungi.

In one embodiment of the host cell descried above, the yeast includes microorganisms that belong to the genus *Saccharomyces*, the genus *Hansemula* or the genus *Pichia*.

In one embodiment of the host cell, described above, the yeast is *Saccharomyces cerevisiae*.

In one embodiment of the host cell described above, the filamentous fungi are microorganisms that belong to the genus *Acremonium*, the genus *Humicola*, the genus *Aspergillus*, the genus *Trichoderma* or the genus *Fusarium*.

In one embodiment of the host cell described above, the filamentous fungi are *Acremonium cellulolyticus, Humicola insolens, Aspergillus niger, Aspergillus oryzae, Trichoderma viride,* or *Fusarium oxysporus*.

The present invention also provides a method for producing the β-glucosidase or its modified protein described above, which includes a step of culturing the host cells described above, followed by collecting the β-glucosidase or its modified protein described above from the host and/or its culture liquid.

The present invention provides a β-glucosidase produced according to the method described above.

The present invention also provides an enzyme composition that contains the β-glucosidase described above.

The present invention also relates to an enzyme composition for improving the processing and/or utilization efficiency of plants or plant-derived substances, which contains the β-glucosidase described above.

The present invention also provides an enzyme composition, which contains the β-glucosidase described above and which acts on glycosides with aglycone linked thereto via β-D-glucopyranosyl linkage for improving the processing and/or utilization efficiency of plants or plant-derived substances.

In one embodiment of the enzyme composition described above, the composition further contains one or more components of cellulase, xylanase, protease, galactanase, galactosidase, arabinanase, arabinofuranosidase, mannagnase, rhamnogalacturonase, polygalacturonase, pectin, methylesterase, pectin lyase and polygalacturonic lyase.

The present invention also provides a feed additive that contains the β-glucosidase or the enzyme composition described above.

The present invention also provides a feed that contains the feed additive described above.

The present invention also provides an enzyme agent for silage, which contains the β-glucosidase or the enzyme composition described above.

The present invention also provides silage that contains the enzyme agent for silage described above.

The present invention provides an enzyme agent for food processing, which contains the β-glucosidase or the enzyme composition described above.

The present invention also provides a processed food that contains the enzyme agent for food processing described above.

BEST MODES OF CARRYING OUT THE INVENTION

Figure 1:
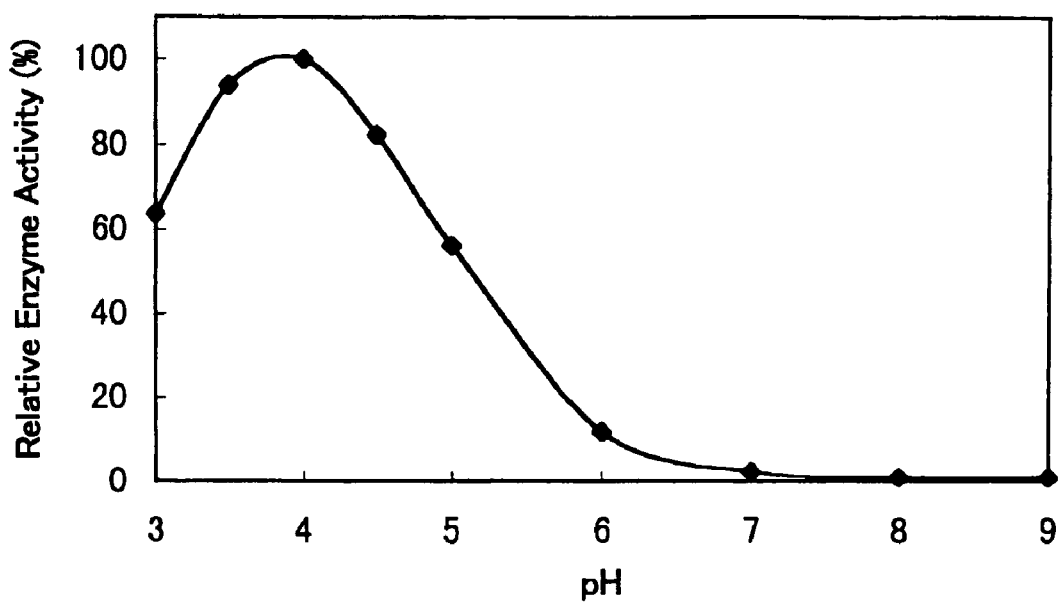
FIG. 1 is a graph showing the optimum pH at 37° C. of the β-glucosidase A obtained in Example 1.

For the microorganisms of producing cellulases that include the β-glucosidase of the invention, there are mentioned filamentous fungi of the genus *Acremonium*. Concretely mentioned are *Acremonium cellulolyticus* Y-94 (deposition number: FERM BP-5826) (transferred from accession number FERM P-6857 deposited on the date of Jan. 12, 1983) and *Acremonium cellulolyticus* TN (deposition number FERMBP-685 ) (transferred from accession number FERM P-7894 deposited on the date of Oct. 13, 1984), both being deposited under international deposition based on the Budapest Treaty in the International Patent Organism Depositary of the National Institute of Advanced Industrial Science and Technology (Central 6, 1-1, Higashi 1-chome, Tsukuba, Ibaraki, Japan). For producing β-glucosidase by the use of these microorganisms, employable is any known method, for example, according to the method described in JP-B 60-43954 and 63-63197, and β-glucosidase is collected from the culture of the microorganisms.

After the microorganisms are cultured, the cultured cells are removed from the resulting culture through centrifugation or the like, and the supernatant thus obtained may be used as a crude enzyme. In general, however, the supernatant is concentrated through ultrafiltration or the like, and an antiseptic is added thereto to prepare a concentrated enzyme; or after concentrated, it is spray-dried into a powdery enzyme.

If desired, the concentrated enzyme or the powdery enzyme may be partially purified or highly purified to obtain the β-glucosidase of the invention.

The purification may be effected in any ordinary manner, for which, for example, concretely employable is salting out with ammonium sulfate or the like, organic solvent precipitation with alcohol or the like; membrane separation, or chromatographic separation with ion-exchange matter, hydrophobic chromatographic carrier, gel permeation carrier or the like. These methods may be effected singly or as combined in any desired manner.

The enzyme of the invention is an enzyme that exhibits a β-glucosidase activity, or that is, β-D-glucoside glucohydrolase EC3.2.1.21. Concretely, it means an enzyme that produces glucose through exoenzymatic hydrolysis of cello-oligosaccharides, cellobiose or glycosides with aglycone linked thereto via β-D-glucopyranosyl linkage.

The first aspect of the invention provides a novel enzyme having a β-glucosidase activity, which is derived from microorganisms of the genus *Acremonium* and has the characteristics as stated in claim 1.

In one preferred embodiment of the invention, the enzyme is obtained from *Acremonium cellulolyticus*. More detailed properties of the enzyme are as follows:

(a) Action and Substrate Specificity:

The enzyme produces glucose through exoenzymatic hydrolysis of cello-oligosaccharides, cellobiose or glycosides with aglycone linked thereto via β-D-glucopyranosyl linkage.

Regarding its substrate specificity, the enzyme is highly active to cello-oligosaccharides and cellobiose. It is also highly active to glycosides with aglycone, such as oligosaccharides and cellobiose. It is also highly active to glycosides with aglycone, such as p-nitrophenyl-β-D-glucopyranoside (hereinafter abbreviated as pNPG), o-nitrophenyl-β-D-glucopyranoside (hereinafter abbreviated as ONPG) or salicin, linked thereto via β-D-glucopyranosyl linkage. Further, it is active to any of β-linked-glucobioses in different bonding linkages (β-1,2; β-1,3; β-1,4; and β-1,6 linkages).

(b) Molecular Weight:

The molecular weight of the enzyme is about 108,000, measured through SDS-polyacrylamide gel electrophoresis.

(c) Isoelectric Point:

The isoelectric point (pI) of the enzyme is about 4.7, measured through polyacrylamide gel isoelectric focusing.

(d) Optimum pH:

The optimum pH of the enzyme for pNPG degradation activity thereof is approximately from 3.5 to 4.0, but the enzyme is highly active at a pH of approximately from 3.0 to 5.5.

(e) Optimum Temperature (Optimum Temperature For Action):

The optimum temperature of the enzyme for pNPG degradation activity thereof is about 70° C., but the enzyme is highly active at a temperature approximately falling between 40 and 77° C.

(f) Degradation Activity:

The pNPG degradation activity of the enzyme is about 240 units/mg protein; and the cellobiose degradation activity thereof is about 370 units/mg protein.

The method of measuring the activity of the enzyme and the definition of one unit of the activity are mentioned below pNPG degradation activity:

At pH 4.0 and at 37° C., the enzyme is made to act on a solution of 4.5 mM pNPG, and the amount of the enzyme needed for producing 1 μmol of p-nitrophenol for 1 minute is defined as one unit.

Cellobiose Degradation Activity:

At pH 4.0 and at 37° C., the enzyme is made to act on a solution of 13.3 mM cellobiose, and the amount of the enzymes needed for producing 1 μmol of glucose for 1 minute is defined as one unit.

Another aspect of the invention provides an enzyme showing a β-glucosidase activity and having the characteristics as stated in claim 3. Specifically, it is a β-glucosidase enzyme that contains a protein of a part of or the 1st to 838th sequence of the amino acid sequence of Sequence ID NO 2 of the Sequence Listing, or contains a modified protein of that amino acid sequence. The α-glucosidase enzyme that contains the amino acid sequence of Sequence ID NO 2 of the Sequence Listing is hereinafter referred to as β-glucosidase A.

In the invention, a part of the amino acid sequence of Sequence ID NO 2 means a partial sequence thereof, for example, having a length utilizable as a probe, and also a part of the partial sequence that still has its β-glucosidase activity.

The invention encompasses a protein that further has a part or all of the —20th to —1st amino acid sequence of Sequence ID NO 2 at the N-terminal side of the above-mentioned protein. In this, the —20th to —1st amino acid sequence of Sequence ID NO 2 is considered as a signal peptide, and thus a part of the sequence means its partial sequence that has its signal peptide activity, and also means a sequence that remains at the N-terminal of the protein as a result of the processing site difference in different types of expression hosts.

The invention further encompasses a modified protein of the above-mentioned protein. The modified protein in the invention means a protein that results from modification such as addition, insertion, removal, deletion or substitution of multiple (e.g., from one to several) amino acids in the amino acid sequence of the above-mentioned protein, still having its β-glucosidase activity.

The enzyme for the invention may be obtained from filamentous fungi, concretely from microorganisms of the genus *Acremonium* (e.g., *Acremonium cellulolyticus*).

The invention also provides a gene that comprises a DNA having the properties as stated in claim 7.

The DNA is any of a DNA that comprises the base sequence of Sequence ID NO 1 of the Sequence Listing; a DNA that includes a modified sequence of the base sequence and codes for a protein having a β-glucosidase activity; and a DNA that codes for a protein with an amino acid sequence of Sequence ID No 2 of the Sequence Listing or for a modified protein thereof.

Once an amino acid sequence of a protein is determined, the DNA that codes for it is readily sequenced, and various base sequences each coding for any of the protein that contains the amino acid sequence of Sequence ID NO 2 and its modified proteins may be selected.

The base sequence in the invention may be any of nature-derived ones or completely synthesized ones, or may also be any ones synthesized from a part of nature-derived ones.

One typical method for obtaining the base sequence for the invention comprises screening base sequences in an

*Acremonium cellulolyticus*-derived chromosome library or cDNA library in an ordinary manner generally employed in the field of genetic engineering, for example, by the use of suitable DNA probes formed on the basis of the information of partial amino acid sequences.

One typical sequence that codes for the amino acid sequence of the β-glucosidase of the invention contains a part or all of the base sequence of Sequence ID NO 1 of the Sequence Listing. The base sequence of Sequence ID NO 1 has an open reading frame (hereinafter abbreviated as ORF) that starts from the 1st to 3rd ATG and ends at the 2575th to 2577th TAA. The base sequence that starts from 61st to 63rd sequence corresponds to the N-terminal amino acid of the above-mentioned matured protein that comprises 838 residues.

In the invention, the transformant of *Escherichia coli* having a plasmid that contains the DNA sequence of Sequence ID NO 1 of the Sequence Listing is now under international deposition based on the Budapest Treaty in the International Patent Organism Depositary of the National Institute of Advanced Industrial Science and Technology (Central 6, 1-1, Higashi 1-chome, Tsukuba, Ibaraki, Japan), and its accession number is FERM BP-7703 (transferred from accession number FERM P-17987 deposited on the date of Aug. 4, 2000).

Further, the invention of claim 7 encompasses a modified sequence of the above-mentioned base sequence. The modified sequence in the invention means a base sequence that hybridizes with the above-mentioned base sequence under a stringent condition and codes for a protein having a β-glucosidase activity. The stringent condition is as follows: A labeled, full-length DNA sequence of Sequence ID NO 1 is used as a probe. After a sample to be identified is prehybridized (42° C.) for 1 hour according to the method of BCL-direct DNA/RNA labeling detection system (by Amersham), the probe is added thereto, and this is further hybridized for 15 hours (42° C.). Next, this is washed twice with one-fold concentration SSC with 0.4% SDS and 6 M urea added thereto (SSC; 15 mM sodium citrate, 150 mM sodium chloride) at 42° C. for 20 minutes, and then further washed twice with 5-fold concentration SSC at room temperature for 10 minutes.

The invention provides an expression vector that contains the DNA sequence of claim 7, for example, the base sequence which codes for a protein that contains the amino acid sequence of Sequence ID NO 2 of the Sequence Listing or its modified protein (hereinafter this is simply referred to as "the DNA sequence of the invention"), in such a condition that it can replicate the DNA sequence in host microorganisms and can express therein the protein coded for by the DNA sequence (claim 12).

The expression vector may be constructed, based on self-replicable vectors, namely, those who exist as extrachromosomal independents and of which the replication does not depends on replication of chromosomes, for example, plasmids. The expression vector may also be such that, when it is introduced into host microorganisms, it is integrated in the genome of the host microorganisms, and it is replicated along with the chromosome integrated with it.

Regarding the process and the method for constructing the vector of the invention, herein employable are those generally employed in the field of genetic engineering.

The expression vector of the invention is actually introduced into host microorganisms to express therein a protein that has the desired activity. For the purpose, it is desirable that the expression vector of the invention contains, in addition to the above-mentioned DNA sequence of the invention, an additional DNA sequence for controlling the protein expression, a genetic marker for selecting the microorganisms, etc. The DNA sequence for expression control includes promoter, terminator, DNA sequence that codes for signal peptide, etc.

The promoter is not specifically defined provided that it has a transcription activity in host microorganisms, and it may be obtained as a DNA sequence that controls the expression of a gene which codes for the same or different type of protein as in the host microorganisms. The signal peptide is not also specifically defined provided that ti contributes to protein secretion in host microorganisms, and it may be obtained from a DNA sequence that is derived from a gene which codes for the same or different type of protein as in the host microorganisms.

The genetic marker in the invention may be suitably in accordance with the method of screening transformants employed herein. For example, a gene that codes for chemical resistance or a gene that compensates for auxotrophy may be utilized for it.

The invention further provides microorganisms (host cells) transformed with the above-mentioned expression vector, as stated in claim 13. The host-vector system is not specifically defined, and, for example, it may be a system that comprises any of coliform bacteria, actinomycete, yeast, filamentous fungi, etc., and may also be a fused protein expression system that comprises any of them fused with any other protein.

Transformation of microorganisms with the expression vector may also be effected in any method generally employed in this technical field.

One preferred embodiment of the invention provides yeast cells capable of expressing the β-glucosidase enzyme which is coded for by the DNA sequence of the invention.

The yeast cells of the invention include, for example, microorganisms that belong to the genus *Saccharomyces*, the genus *Hansenula* or the genus *Pichia*, for example, those of *Saccharomyces cerevisiae*, etc.

For the microorganisms capable of expressing the β-glucosidase enzyme which is coded for by the DNA sequence of the invention, also provided herein are filamentous fungi that belong to imperfect fungi.

The filamentous fungi in the invention include microorganisms that belong to the genus *Acremonium*, the genus *Humicola*, the genus *Aspergillus*, the genus *Trichoderma* or the genus *Fusarium*. Their preferred examples are *Acremonium cellulolyticus, Humicola insolens, Aspergillus niger, Aspergillus oryzae, Trichoderma viride, Fusarium oxysporus*, etc.

When the transformant is cultured in a suitable medium, and the above-mentioned protein of the invention (β-glucosidase or its modified protein) may be isolated from the culture (claim 19). Specifically, still another aspect of the invention provides a method for producing the novel protein of the invention.

The culture of the transformant and the condition for it may be substantially equivalent to those for the microorganisms used. For recovering the intended protein from the transformant culture, herein employable in any known method that is generally employed in this technical field.

For producing the β-glucosidase enzyme of the invention by the use of filamentous fungi, *Acremonium cellulolyticus*, for example, employable is the method described in JP-A 2001-17180.

Concretely, a recombinant vector for gene expression, which has a β-glucosidase gene linked downstream to the promoter of obh1 gene that is expressed most highly in

*Acremonium cellulolyticus*, is constructed, and this vector is introduced into *Acremonium cellulolyticus*, whereby the resulting transformant can express a large amount of β-glucosidase protein therein.

Still another aspect of the invention provides an enzyme composition, that contains the above-mentioned β-glucosidase enzyme of the invention or the modified protein, as stated in claim 21.

The enzyme composition of the invention may be produced by mixing the β-glucosidase enzyme of the invention or its modified protein with ordinary components that are generally in enzyme compositions, for example, vehicle (e.g., lactose, sodium chloride, sorbitol, etc.) surfactant, antiseptic, etc.

The morphology of the enzyme composition of the invention may be any desired one, and the composition may be formulated in any desired morphology, for example, as powder or liquid.

The β-glucosidase obtained according to the invention has an excellent ability to liberate glucose and is suitable for improving the processing or utilization efficiency of plants or plant-derived substances that contain cellulose, cello-oligosaccharides, cellobiose and/or glycosides with aglycone linked thereto via β-D-glucopyranosyl linkage. Specifically, cellulose, cello-oligosaccharides, cellobiose and/or glycosides with aglycone linked thereto via β-D-glucopyranosyl linkage are hydrolyzed with the β-glucosidase enzyme or the enzyme composition of the invention, whereby the plants or plant-derived substances that contain them may be processed and/or utilization efficiency thereof may be improved.

According to the invention, herein obtained are such β-glucosidase enzyme and the enzyme composition which are characterized in that they can hydrolyze cellulose, cello-oligosaccharides, cellobiose and/or glycosides with aglycone linked thereto via β-D-glucopyranosyl linkage, and which are for improving the processing and/or utilization efficiency of plants or plant-derived substances that contain cellulose, cell-oligosaccharides, cellobiose and/or glycosides with aglycone linked thereto via β-D-glucopyranosyl linkage.

Plants or plant-derived substances that contain cellulose, cello-oligosaccharides, cellobiose and/or glycosides with aglycone linked thereto via β-D-glucopyranosyl linkage may be processed with the enzyme composition to give enzyme-processed products.

Regarding the plants, the invention may apply to all plants or their cut pieces, etc. As to the plant-derived substances, the invention may apply to all plant-derived substances that include plant tissues such as cell walls, skin tissues, etc. and plant tissue-derived substances; extracted components such as cell contents, various glycoproteins and glycolipids, aromatic components, pigments, etc.

Concretely, the invention is directed to grass, vegetables, fruits, etc. in the field of feed and the field of food, and may also apply to their processed substances, juice, puree, paste, squeezed leavings, and extracted leavings. In addition, the invention is utilizable for promoting the saccharification of cellulose biomass into glucose and for improving the processing efficiency of wastes of cellulose-containing products such as paper, etc.

The glycosides with aglycone linked thereto via β-D-glucopyranosyl linkage include various phenol glycosides, nitrile glycosides, coumarin glycosides, anthracene glycosides, steroid glycosides (saponin substances), terpene glycosides, amaroidal glycosides, flavone glycosides, isoflavone glycosides, flavonol glycosides, flavanone glycosides, pelargonidin glycosides, cyanidin glycosides, delphinidin glycosides, triterpenoidglycosides, cardiac glycosides and the like that are widely distributed in the vegetable kingdom.

The invention further provides an enzyme composition prepared by adding one or more components of cellulase, xylanase, protease, galactanase, arabinanase, arabinofuranosidase, mannanase, rhamnogalacturonase, polygalacturonase, pectin methylesterase, pectin lyase and polygalacturonic lyase, to the β-glucosidase enzyme or the enzyme composition as above.

As compared with the enzyme composition that contains β-glucosidase enzyme alone, the enzyme composition of the type could further improve the processing and utilization efficiency of plants or plant-derived substances.

When the β-glucosidase enzyme or the enzyme composition of the invention is incorporated into feed for animals, it improves the digestibility of β-glucan in feed. In a different viewpoint, it degrades β-glucan to thereby promote the utilization of protein accumulated in feed. Accordingly, the invention further provides a feed additive that contains the β-glucosidase enzyme or the enzyme composition, and also a method of adding the feed additive to feed. The method includes a step of processing the raw materials for feed with the β-glucosidase enzyme or the enzyme composition of the invention.

In addition, it has been found that, when the β-glucosidase enzyme or the enzyme composition of the invention is added to silage, then it significantly improves the fermented quality of silage. Accordingly, the invention further provides an enzyme preparation for silage that contains the β-glucosidase enzyme or the enzyme composition. If desired, the enzyme preparation for silage may be combined with a preparation that comprises lactic acid bacteria of the genus *Lactobacillus, Streptococcus, Lactococcus, Pediococcus* or the like, and/or a preparation that comprises acid-producing bacteria of the genus *Propionibacterium* or the like. The combined compositions may attain further quality improvement owing to the synergistic effect thereof.

The invention further provides a method for producing silage by the use of the enzyme agent for silage, and provides the silage produced according to the method. It is directed to any and every ordinary material for silage that includes grass, feed crops, side products in production of food and the like, side products in agriculture, feed, etc.

For the grass for use herein, for example, gramineous grass includes timothy, orchard grass, Italian rye grass, perennial rye grass, meadow fescue, guinea grass, etc.; and leguminous grass includes alfalfa, clover, etc.

Next, the feed crops for use herein are corn, sorghum, barley, rye, rye whet, etc.

The side products in production of food and the like for use herein are blackstrap molasses, vinegar lees, beer lees, soybean cake lees, orange lees, shochu lees, etc. The side products in agriculture for use herein are wheat (barley) straws, beat tops, beat pulp, etc.

The feed for the raw material for silage includes simple feed, compound feed and thick feed that are generally used for fermented feed, as well as mixed feed of such feed with other crude feed.

When the β-glucosidase enzyme or the enzyme composition of the invention is used for food processing, its advantages are that the aromatic component of juice, wine and the like increases, juice is clarified, its viscosity lowers, its color betters and its bitterness is removed, and the fermentation yield in brewing and baking increases,. In addition, the quality including the aroma, the color and the taste of food is improved.

Accordingly, the invention further provides an enzyme agent for food processing that contains the β-glucosidase enzyme or the enzyme composition. In addition, the invention further provides a method for food processing by the use of the enzyme agent for food processing, and provides food processed according to the method.

Since the β-glucosidase enzyme and the enzyme composition of the invention have a high activity of hydrolyzing β-D-glucoside, it can be utilized for reagents for clinical checkups for amylase activity measurement.

Regarding the method of using the enzyme and the enzyme composition of the invention, they may be used under the conditions of pH and temperature that are generally employed in various fields mentioned above. In view of the properties of the enzyme, they may be used generally at a pH falling between 3.0 and 6.0 and at a temperature falling between 10 and 80° C., more preferably at a temperature falling between 30 and 80° C. Regarding the amount of the enzyme to be used, the dose thereof may be so determined that the enzyme attains its object with time, and the enzyme in that condition attains satisfactory results.

The invention is described in more detail with reference to the following Examples, which, however, are not intended to restrict the scope of the invention.

EXAMPLE 1

Purification Of β-Glucosidase A (1) Preparation of Crude Enzyme Powder

To obtain crude powder of β-glucosidase from microorganisms of the genus *Acremonium*, said microorganisms were cultured according to the process mentioned below. All the media used herein comprise the components mentioned below, and they were sterilized under heat in an ordinary manner.

Medium Composition

Cotton seed oil lees 2%; cellulose 2%, dipotassium hydrogenphosphate 1.2%; bactopeptone 1%; potassium nitrate 0.6%; urea 0.2%; potassium chloride 0.16% magnesium sulfate 7-hydrate 0.001%; cupper sulfate 5-hydrate 0.001% (pH 4.0).

Calls of *Acremonium cellulolyticus* Y-94 (FERM BP-5826) were inoculated into 500 ml of the medium, and cultured at 30° C. for 48 hours with stirring. Next, the resulting culture broth was used as a seed, and the medium was scaled up to 15 liters. With further scaling up the medium, the amount of the culture in a 600-liter tank was finally 300 liters. In the tank, the cells were subjected to a spinner culture under seration for 7 days.

The resulting culture was filtered through a filter press, and then concentrated to 15 liters through ultrafiltration. Then, 2 kg of lactose was added thereto, and this was spray-dried into powder. The yield of the crude β-glucosidase powder obtained according to this method was 5.0 kg.

(2) Purification of β-Glucosidase A

The crude powder obtained in the above (1) was dissolved in an acetate buffer (pH 4.5), and the impurities were removed through high-performance cooling centrifugation. The resulting supernatant is the starting material for purification of enzyme, and it was purified according to the method mentioned below.

(a) Weak basic anion-exchange chromatography: The supernatant was absorbed by DEAE Sepharose FF (by Pharmacia) with Tris-HCl buffer (0.01 M, pH 7.5), and subjected to linear gradient elution with Tris-HCl buffer (0.01 M, pH 7.5) containing from 0 M to 0.1 M of NaCl to thereby fractionate the fraction that indicated β-glucosidase.

(b) Affinity chromatography: The β-glucosidase active fraction obtained in the above (a) was adsorbed by Chelating Sepharose FF (by Pharmacia) having a ligand of $CU^{2+}$ bonded. thereto, using a phosphate buffer (0.025 M, pH 7.0) with 0.1 M NaCl therein, and subjected to linear gradient elution from pH 7.0 to pH 2.5 with the 0.1 M NaCl-containing phosphate buffer (0.025 M). The fraction that indicated β-glucosidase activity was again applied to Chelating Sepharose FF to obtain the fraction still indicating β-glucosidase activity.

(c) Hydrophobic chromatography: The 1-glucosidase fraction obtained in the above (b) was adsorbed by Butyl Toyopearl 650 M (by Tosoh), using Tris-HCl buffer (0.05 M, pH 7.0) with 1 M $(NH_4)_2SO_4$ therein, and subjected to linear gradient elution with Tris-HCl buffer (0.05 M, pH 7.0) containing from 1 M to 0 M of $(NH_4)_2SO_4$ to thereby fractionate the fraction that indicated β-glucosidase activity.

(d) Gel permeation chromatography: The β-glucosidase activity fraction obtained in the above (c) was passed through Superdex 75 (by Pharmacia), using a phosphate buffer (0.025 M, pH 7.0) with 0.1 M NaCl therein, to fractionate the fraction that indicated β-glucosidase activity.

(e) Isoelectric chromatography: The β-glucosidase active fraction obtained in the above (d) was adsorbed by MonoP (by Pharmacia) with an imidazole-acetate buffer (0.025 M, pH 6.2), and eluted with 10-fold diluted Polybuffer 74 (by Pharmacia) (pH 3.8) to fractionate the fraction that indicated β-glucosidase activity (β-glucosidase A).

EXAMPLE 2

Enzymatic And Proteinaceous Properties of β-Glucosidase A (1) Substrate Specificity, Action Characteristics The purified β-glucosidase A that had been obtained in Example 1 was analyzed for its activity to various substrates. Concretely, the enzyme was made to act on 2-meric to 5-meric cello-oligosaccharides, and it produced glucose from all of them. On the other hand, the enzyme was made to act on pNPG, ONPG and salicin, and it produced glucose from all these substrates. When the enzyme was made to act on β-linked-glucobioses in different bonding linkages (β-1, 2; β-1,3; β-1,4; and β-1,6 linkages), it produced glucose from all these substrates.

(2) Optimum pH

The optimum pH at 37° C. of the β-glucosidase A obtained in Example 1 is shown in FIG. 1. In a phosphate buffer, the enzymes showed the highest activity at a pH of from 3.5 to 4.0.

(3) Optimum Temperature (Optimum Temperature for Action)

Figure 2:
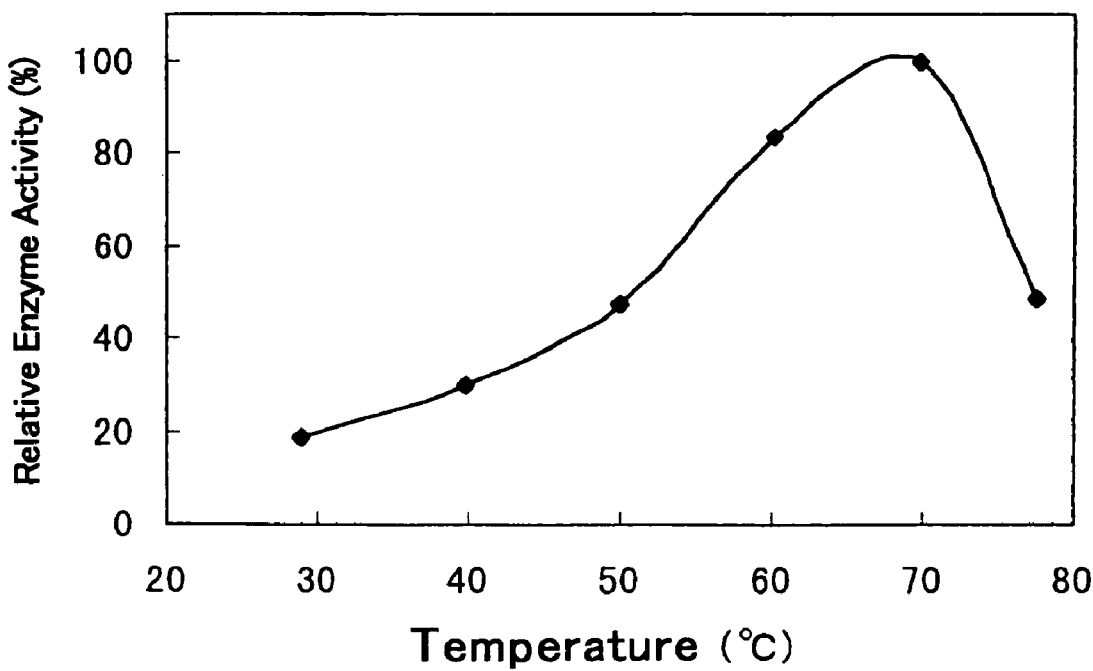
FIG. 2 is a graph showing the optimum temperature of the β-glucosidase A obtained in Example 1.

To confirm the optimum temperature for action of the β-glucosidase A obtained in Example 1, the enzyme was analyzed for its pNPG degradation activity in an acetate buffer (0.05 M, pH 4.0). As in FIG. 2, the optimum temperature of the enzyme was 70° C.

(4) Molecular Weight

To determine the molecular weight of the β-glucosidase A obtained in Example 1, the enzyme was subjected to SDS-polyacrylamide gel electrophoresis (8% gel, by Tefco).

As a result, the molecular weight of the β-glucosidase A was calculated to be about 108,000.

The molecular weight of the standard samples used in this test is as in Table 1.

TABLE 1

| | |
|---|---|
| Myosin | 200,000 |
| β-Galactosidase | 116,300 |
| Phosphorylase b | 97,400 |
| Serum albumin | 66,200 |
| Ovalbumin | 45,000 |

(5) Isoelectric Point

To determine the isoelectric point (pI) of the β-glucosidase A obtained in Example 1, the enzyme was subjected to polyacrylamide gel isoelectric focusing (pH 3.0 to 10.0, by Tefco)

As a result, the isoelectric point of the β-glucosidase A was calculated to be 4.7.

The isoelectric point of the standard samples used in this test is as in Table 2.

TABLE 2

| | |
|---|---|
| Trypsinogen | 9.3 |
| Lentil lectin-basic band | 8.7 |
| Lentil lectin-middle band | 8.5 |
| Lentil lectin-acidic band | 8.2 |
| Horse myoglobin-basic band | 7.4 |
| Horse myoglobin-acidic band | 6.9 |
| Human carbonic anhydrase B | 6.6 |
| Bovine carbonic anhydrase B | 5.8 |
| β-Lactoglobulin A | 5.2 |
| Soybean trypsin inhibitor | 4.6 |
| Amyloglucosidase | 3.5 |

EXAMPLE 3

Amino Acid Sequence Of β-Glcosidase A (1) N-Terminal Amino Acid Sequence

The purified β-glucosidase A that had been obtained in Example 1 was sequenced at its N-terminal amino acid residues. Using 8% Gel SDS-PAGE mini (by Tefco), each sample was subjected to electrophoretic separation, then transcribed onto a Miniproblot membrane (by Perkin Elmer) with Horizeblot (by Atto), stained with Coomassie Brilliant Blue R-250 (by Nacalai Tesque), then washed with 50% methanol and dried with air. From this, the band with a protein blot to have a molecular weight of 108,000 was cut out, and applied to a protein sequencer, Procise 491 (by Perkin Elmer) to sequence the N-terminal amino acid residues of the enzyme.

15 N-terminal amino acid residues of the β-glucosidase A were sequenced, and their sequence is as in Sequence ID NO 3 of the Sequence Listing.

(2) Partial Amino Acid Sequence of β-Glucosidase A

A sample of the purified β-glucosidase A that had been obtained din Example 1 was reductively carboxymethylated and then processed with lysyl endopeptidase. The degraded product was applied to μ-blotter, ABI 173A (by Perkin Elmer) for separation, and was blotted on a PVDF membrane (by Perkin Elmer). The resulting peptide fragments were sequenced with the above-mentioned protein sequencer. Thus sequenced, the partial amino acid sequence L-4 of the β-glucosidase A is as in Sequence ID NO 4 of the Sequence Listing, and L-5 thereof is as in Sequence ID NO 5.

EXAMPLE 4 cDNA Cloning Of β-Glucosidase A (1) Isolation of mRNA of *Acremonium cellulolyticus* and Formation of cDNA Library Thereof:

Cells of *Acremonium cellulolyticus* Y-94 (FERM HP-5826) were cultured in a cellulase induction medium (4% cellulose, 1% peptone, 0.6% potassium nitrate, 0.2% urea, 0.16% potassium chloride, 0.12% magnesium sulfate, 1.2% monopotassium phosphate, 0.001% zinc sulfate, 0.001% manganese sulfate and 0.001% copper sulfate (pH 4.0) at 32° C. for 4 days. The cells were recovered through centrifugation.

The resulting cells were frozen with liquid nitrogen, freeze dried and the ground in a mortar with a pestle. From the thus-ground cells, a total RNA was isolated using ISOGEN (by Nippon Gene) and according to the protocol attached to it. Further, from the total RNA, its mRNA was purified using mRNA Purification Kit (by Pharmacia) and according to the protocol attached to it.

From the thus-obtained mRNA, its cDNA was synthesized using Time SAVER cDNA Synthesis Kit (by Pharmacia) and according to the protocol attached to it. The cDNA was inserted into a phage vector Lambda ZAP II (by Stratagene).

Thus constructed, the recombinant phage vector was subjected to in-vitro packaging, using Gigapack III Gold Packaging Extract (by Stratagene) and according to the manual attached to it. Next, cells of *Escherichia coil* XL1-Blue MRP were infected with the recombinant phage, and cultured on a plate to form plaques.

Thus formed, the cDNA library included $5.5 \times 10^5$ plaque forming units. Further, the cDNA library was amplified according to the protocol attached to Lambda ZAP II. Cells of *Escherichia coli* XL-1 Blue MRF' were injected with the recombinant phase in the thus-amplified cDNA library, and cultured on a plate to form plaques.

(2) DNA Amplification Through PCR

Using the cDNA prepared in the above (1) as a template, DNA fragments were amplified in a process of PCR (polymerase chain reaction ), based on the information of the partial amino acid sequences of the β-glucosidase A as in Example 3.

For each primer, prepared were synthetic oligonucleotides (Sequence ID NO 6 and 7) corresponding to the partial amino acid sequences (1st to 6th residues of Sequence ID NO 4, and 3rd to 8th residue of Sequence ID NO 5) of the peptides L-4 (Sequence ID NO 4) and L-5 (Sequence ID NO 5), respectively.

PCR was effected in 50 μliters of the reaction solution, using 50 ng of the cDNA as the template, 1.25 units of Taq DNA polymerase (by Takara Shuzo) and the buffer attached to it, dNTP Mixture, and 1 μM of the above-mentioned primer, under the condition mentioned below.

After pre-treated at 94° C. for 10 minutes, this was subjected to 30 cycles of reaction. One reaction cycle comprises a denaturation step at 94° C. for 1 minute, an annealing step at 48° C. for 1 minute and an extension step at 72° C. for 1 minute. Next, this was incubated at 72° C. for 2 minutes to finish the reaction. The reaction amplified the DNA fragment to about 600 bp.

(3) Subcloning of PCR Product

The DNA fragment of about 600 bp that had been amplified through the previous PCR was collected with GENELUTE MINUS EtBr SPIN COLUMNS (by Sigma), and this was linked to a vector pUC118 (by Takara Shuzo), using a DNA ligation kit Ver. 1 (by Takara Shuzo). Competent cells (E. coli competent cells JM109, by Takara Shuzo) were transformed with the resulting linked mixture. Next, the resulting transformant cells were cultured, and then the plasmid DNA thereof was recovered, using QLAprep Spin Miniprep Kit (by Qiagen) and according to the protocol attached to it.

The resulting plasmid DNA was cleaved with multiple restriction endonucleases and then subjected to 0.7% agarose gel electrophoresis to selected the plasmid DNA, with the fragment of about 600 bp inserted therein. The plasmid with the intended PCR product subcloned is referred to as pABG01.

(4) Base Sequence Analysis Of Plasmid pABG01

Thus cloned, the DNA fragment was sequenced using Autolead Sequencing Kit (by Pharmacia Biotec) and A. L. F. DNA. Sequencer II (by Pharmacia Biotec) and according to the protocols attached to them.

The decoded base sequence was translated into an amino acid sequence, of which one reading frame was found to coincide also with the sequence including the part other than those used as primers for the partial amino acid sequences of the β-glucosidase A, L-4 and L_5, shown in Example 3. This confirms that the base sequence is a part of the gene that codes for the intended β-glucosidase A protein.

Accordingly, the insert DNA contained in this plasmid pABG01 is used as the probe for screening in the subsequent process.

(5) Screening Through Plaque Hybridization

The insert DNA fragment was cut out of the plasmid pABG01 obtained in the above (3), and this was labeled using ECL Direct DNA/RNA Labeling Detection System (by Amersham) and according to the protocol attached to it.

Next, the phage plaque produced in the previous (1) was transferred onto Hybond-N+ nylon transfer membrane (by Amersham) and processed with an alkali of 0.4 N sodium hydroxide so that the recombinant phage DNA on the membrane was denatured into a single-stranded one, which was then washed with 5×SSC (1×SSC: 15 mM sodium citrate, 150 mM sodium chloride) and then dried in air. Thus, the DNA was fixed.

Next, according to the protocol attached to the kit, this was hybridized and processed for detection. Its picture was taken on a Fuji medical X-ray film (by Fuji Photo Film), in which 13 positive phage clones were found.

(6) Preparation Of Phage DNA

From the positive phase clones, the DNA was prepared as a plasmid DNA according to the protocol attached to Phage Vector λ ZAP II.

From ampicillin-resistant E. coli SOLR strain, prepared was a plasmid of pBluescript SK(-) cloned with a DNA fragment. Serving as a template, the plasmid was subjected to PCR with the same primers of L-4 and L-5 as those used in the previous (2) under the same condition as hereinabove.

As a result, an amplified DNA fragment of about 600 bp was obtained in 8 plasmids. Accordingly, it was anticipated that the intended DNA would be cloned in these plasmids, and the size of the insert fragment in these plasmids were determined. One clone contained a DNA fragment of about 2.9 kbp that would include all the region thereof.

(7) cDNA Sequencing

Using primers for T3 and T7 sequencing, the DNA fragment of about 2.9 kbp that had been inserted into the positive recombinant pBluescript SK(-)plasmid obtained in the above (6) was sequenced in the same manner as hereinabove.

As a result, the base sequence contained an open reading frame (ORF) of 2577 bp, and its base sequence is as in Sequence ID NO 1 of the Sequence Listing.

The N-terminal amino acid sequence after the 21st amino acid of the protein estimated from the ORF was analyzed in an ordinary manner, and it corresponded to the N-terminal amino acid sequence of the β-glucosidase A sequenced in Example 3 (1) and to the internal amino acid sequence of the β-glucosidase A sequenced in Example 3(2). Accordingly, it has become obvious that the present gene codes for β-glucosidase A.

From this finding, in addition, it was considered that the starting 1st to 20th amino acid residues of the ORF, or that is, the amino acid sequence of from —20th to —1st amino acid residues would be a signal sequence for extracellularly secreting the β-glucosidase A protein. Further, in the Sequence ID NO 1 of the Sequence listing, the 1st to 838th amino acid sequence codes for the above-mentioned matured protein.

(8) Strain Deposition

The transformant E. coli strain which has the plasmid pBluescript SK (-) with the cDNA fragment of about 2.9 kbp that codes for β-glucosidase A is named Escherichia coli ACCbg101. This strain was deposited under international deposition based on the Budapest Treaty in the International Patent Organism Depositary of the National Institute of Advanced Industrial Science and Technology (Central 6, 1-1, Higashi 1-chome, Tsukuba, Ibaraki, Japan), and its accession number is FERM BP-7703 (transferred from accession number FERM P-17987 deposited on the date of Aug. 4, 2000).

EXAMPLE 5

Over Expression of β-Glucosidase A Gene Derived From *Acremonium Cellulolyticus*

(1) Construction of Recombinant Vector For Expression of β-Glucosidase A Gene

Figure 3:
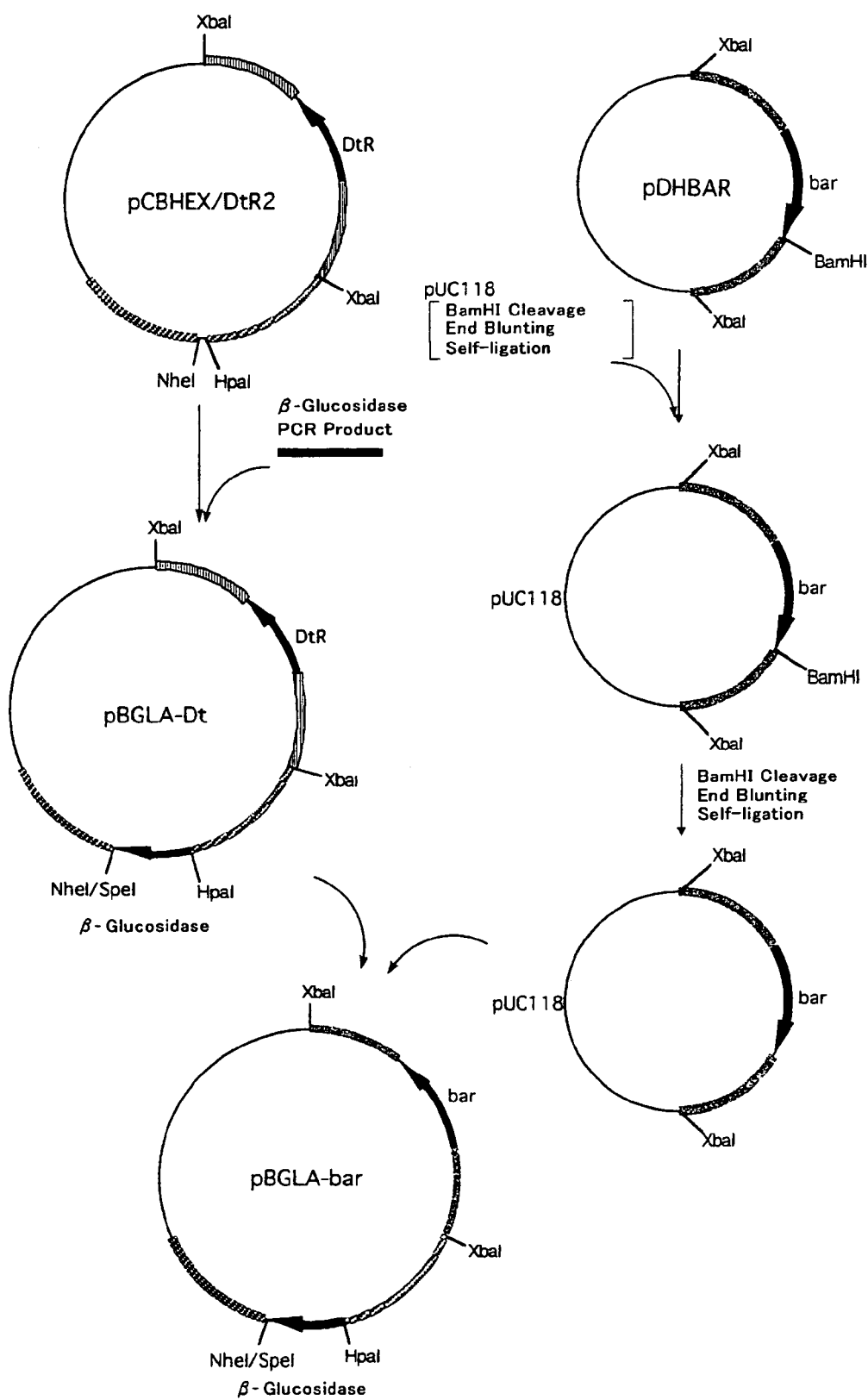
FIG. 3 shows a scheme for constructing the plasmid pBGLA-bar shown in Example 5.

The outline of the process of this Example is shown in FIG. 3.

Serving as a template, the plasmid pABG01 with the β-glucosidase A cDNA inserted therein that had been obtained in Example 4(3) was subjected to PCR with primers of Sequence ID NO 8 and Sequence ID NO 9 of the Sequence Listing. PCR was effected in 50 μ-liters of the reaction solution, using 2.5 units of KOD DNA polymerase (by TOYOBO), buffer #1 attached to it, 0.2 mM dNTP mixture, 1 mM $MgCl_2$, 20 mg of the plasmid DNA and 0.6 μM of the above-mentioned primers, under the condition mentioned below.

After pre-treated at 98° C. for 10 minutes, this was subjected to 10 cycles of reaction. One reaction cycle comprises a denaturation step at 98° C. for 15 seconds, an annealing step at 55° C. for 2 seconds and an extension step at 74° C. for 30 seconds.

The resulting PCR liquid was precipitated with ethanol, and the PCR product was recovered. This was cleaved with restriction endonucleases HpaI and SpeI, and the resulting fragment was inserted between HpaI and NheI of destomycin-resistant cassette-containing pCBHEX/DtR2 described in JP-A 2001 -17180 to construct a plasmid pBGLA-Dt.

The BamHI site of a plasmid pUC118 (by Takara Shuzo) was cleaved. The cleaved site was blunted at its end, and again self-ligated to construct a plasmid pUC118 not having the BamHI site. Into the XbaI site of this plasmid, inserted was a bialaphos-resistant cassette that had been cut out of a plasmid pDHBAR (Watanabe, M. et al., (1999) Appl. Environ. Mircobiol., 65: 1036-1044) with a restriction endonuclease XbaI. This plasmid was cleaved with a restriction endonuclease BamHI. The cleaved site was blunted, and again self-ligand to construct a biarafos-resistant cassette-containing plasmid not having the BamHI site.

The biarafos-resistant cassette was cut out of this plasmid, using a restriction endonuclease XbaI, and this was substituted with the destomycin-resistant cassette in the previously-constructed plasmid pBGLA-Dr at its XbaI site to thereby construct a plasmid pBGLA-bar for protein expression.

(2) Introduction Of β-Glucosidase A Gene Into Host

Cells of *Acremonium cellulolyticus* Y-94 were cultured in an (S) medium (2% Nutrient broth, 0.5% yeast extract and 2% glucose) at 30° C. for 16 hours, and then collected through centrifugation at 3500 rpm for 10 minutes.

The thus-collected cells were washed with 0.5 M sucrose, and then suspended in a protoplast-forming enzyme solution (10 mg/ml chitinase, 10 mg/ml zymolyase, 30 mg/ml β-glucuronidase and 0.5 M sucrose) that had been filtered through a 0.45 μm filter. This was shaken at 30° C. for 60 to 90 minutes so that the hypha thereof was processed into protoplast. The resulting suspension was filtered through absorbent cotton and then centrifuged at 2500 rpm for 10 minutes to recover the protoplast. This was then washed with SUTC buffer (0.5 M sucrose, 10 mM calcium chloride and 10 mM Tris-HCl (pH 7.5)).

The protoplast thus prepared in the manner as above was suspended in 100 μliters of SUTC buffer, to which was added a solution (10 μliters) of 10 μg of the plasmid pBGLA-bar, and this was left on ice for 5 minutes. Next, 400 μliters of PEG solution (60% PEG 4000, 10 mM calcium chloride and 10 mM Tris-HCl (pH 7.5) was added to it, and this was put in ice for 20 minutes. Then, 10 ml of SUTC buffer was added therein, and this was centrifuged at 2500 rpm for 10 minutes. The protoplast thus separated through centrifugation was suspended in 1 ml of SUTC buffer, then again centrifuged at 4000 rpm for 5 minutes, and finally suspended in 100 μliters of SUTC buffer.

The protoplast thus processed in the manner as above was layered on biarafos (1000 μg/ml)-added (A) agar medium (3.9% potato dextrose agar medium (by Nissui Pharmaceutical), 17.1% sucrose), along with an (A) soft agar medium (1.3% potato dextrose agar medium (by Nissui Pharmaceutical), 17.1% sucrose), and cultured at 30° C. for 5 to 9 days in that condition. The colonies formed were collected as transformants.

Figure 4:
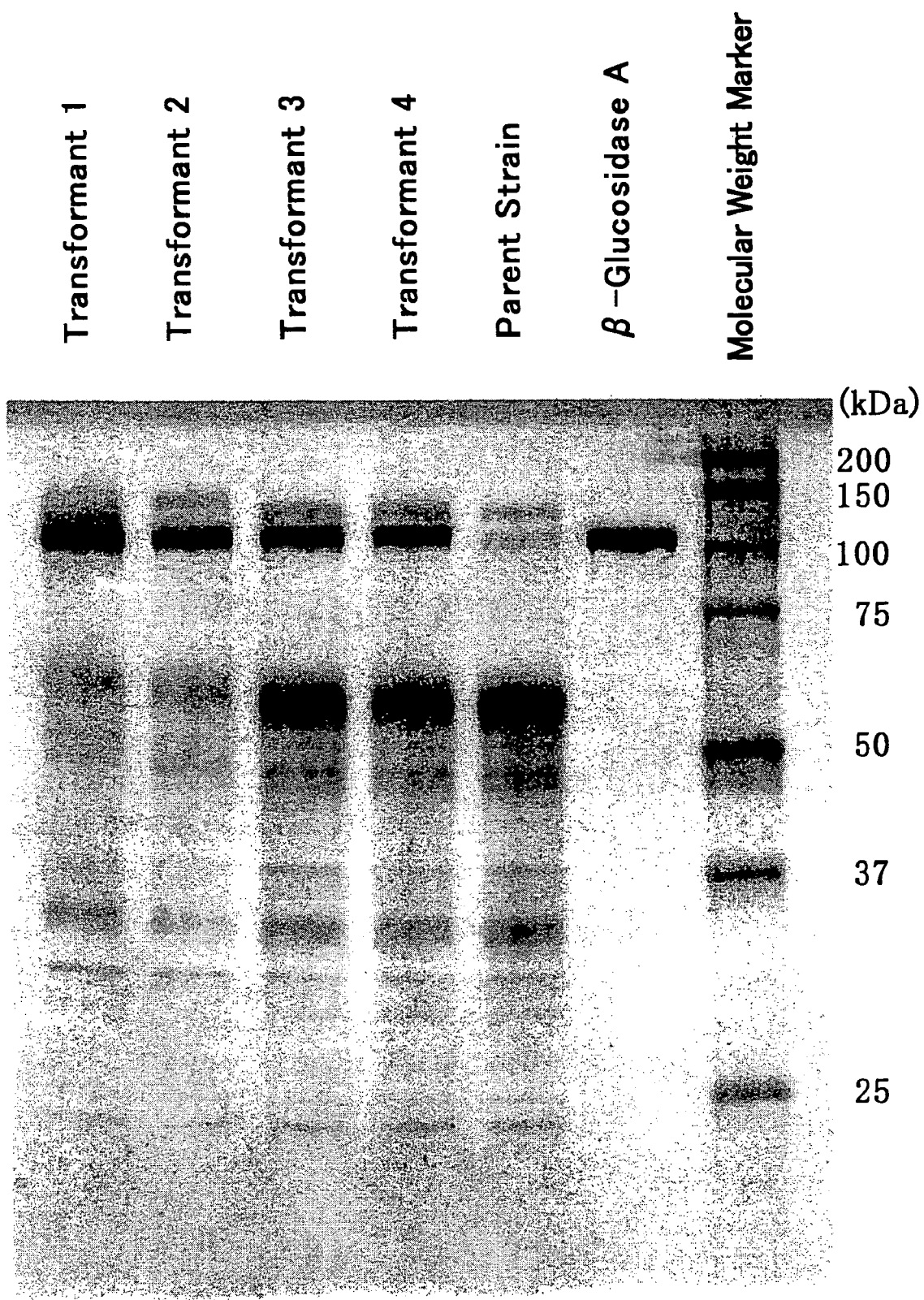
FIG. 4 shows the results of electrophoresis that confirms the expression of β-glucosidase A in *Acremonium cellulolyticus* transformant.

(3) Expression Of β-Glucosidase A in *Acremonium cellulolyticus* Transformant, And Determination Of The Enzyme Activity Of the transformants obtained in (2), best four strains of higher biarafos resistance were selected, and cultured in the cellulase induction medium mentioned above (described in Example 4(1). Each culture supernatant was analyzed with SDS-polyacrylamide gel (SDS-PAGE), and the amount of the β-glucosidase A enzyme secreted by the transformants was higher than that secreted by its parent strain, as in FIG. 4.

The β-glucosidase activity was determined in terms of the cellobiose degradation activity, and it is expressed as the activity (U/ml) power one ml of the culture supernatant. The data are as in Table 3. As is obvious from the Table, the activity of the transformant was up to about 25 times that of the parent strain.

TABLE 3

|  | β-Glucosidase Activity (U/ml) |
| --- | --- |
| Parent strain | 43 |
| Transformant 1 | 1068 |
| Transformant 2 | 665 |
| Transformant 3 | 572 |
| Transformant 4 | 575 |

EXAMPLE 6

For application of the β-glucosidase of the invention to silage, the following test was carried out.

Timothy (variety: Hokuoh) that is generally used as grass was cultivated and harvested, and cut into pieces of from 2 to 3 cm long. The water content of the thus-cut timothy pieces was about 70%. Next, the pure β-glucosidase A that had been produced in Example 1 was sprayed on the surface of the timothy pieces, using a spray device (Jackson's pharyngeal anesthetization spray, by Igarashi Medical Industry). The does of the pure β-glucosidase A to the unit weight of the timothy pieces was from 0.023 to 0.117 units.

50 g of the pure β-glucosidase A-added timothy pieces were packed in a polyvinyl bag in vacuum, and kept at 25° C. for 4 weeks to prepare silage. 150 ml of deionized water was added to the silage and kept at 5° C. overnight, and the pH of the resulting supernatant was measured. The pH data are as in Table 4.

TABLE 4

| Group | Dose of β-glucosidase (unit/g of grass) | pH of Silage |
| --- | --- | --- |
| Control Group | 0 | 5.6 |
| Test Group 1 | 0.023 | 5.5 |
| Test Group 2 | 0.059 | 5.0 |
| Test Group 3 | 0.117 | 4.9 |

As is obvious from the Table, the pH of the silage in all the test groups in which the pure β-glucosidase was added to the grass is lower than that in the control group in which the enzyme was not added, and the pH of the silage decreased dependently upon the dose of the β-glucosidase added to the grass. In this connection, it is said that the fermented quality of silage having a lower pH is better.

The above confirms that β-glucosidase is effective for improving the fermented quality of silage.

INDUSTRIAL APPLICABILITY

The invention provides a novel *Acremonium*-derived β-glucosidase, a gene that codes for the enzyme, an expression vector that contains the gene, and host cells that have been transformed with the expression vector. It also provides an efficient method for producing the novel β-glucosidase.

The invention further provides a technique of utilizing the β-glucosidase or a composition that contains the enzyme for processing plants or plant-derived substances, and the enzyme and the enzyme composition are expected to have various applications in the field of feed, food, etc.

The invention claimed is:

1. An enzyme having β-glucosidase activity, which is isolated from *Acremonium cellulolyticus* and has the following characteristics:
   (a) substrate specificity, action characteristics: acts on cello-oligosaccharides and on glycosides with aglycone linked thereto via β-D-glucopyranosyl linkage to produce glucose;
   (b) molecular weight: 108,000 by SDS-polyacrylamide gel electrophoresis;
   (c) isoelectric point: pI 4.7 by polyacrylamide gel isoelectric focusing;
   (d) optimum pH: between pH 3.5 and 4.0;
   (e) optimum temperature for action: 70° C.; and
   (f) comprises amino acids 1 to 838 of the amino acid sequence of SEQ ID NO: 2 of the Sequence Listing.

2. An isolated or purified β-glucosidase which is isolated from *Acremonium cellulolyticus* having the following characteristics (a) or (b);
   (a) a protein that comprises the 1st to 838th amino acids in the amino acid sequence of SEQ ID NO: 2 of the Sequence Listing;
   (b) the protein (a) which further comprises the —20th to —1st amino acids in the amino acid sequence of SEQ ID NO: 2 of the Sequence Listing, at its N-terminal side.

3. An isolated polynucleotide which is isolated from *Acremonium cellulolyticus* comprising the following DNA (a) or (b);
   (a) a DNA comprising the base sequence of SEQ ID NO: 1 of the Sequence Listing;
   (b) a DNA coding for a protein that comprises the amino acid sequence of SEQ ID NO: 2 of the Sequence Listing.

4. A DNA construct that comprises the polynucleotide of claim 3.

5. An expression vector that contains the DNA construct of claim 4.

6. An isolated host cell transformed with the DNA construct of claim 4.

7. An isolated host cell transformed with the expression vector of claim 5.

8. The host cell as claimed in claim 6 wherein the host is any of coliform bacteria, yeast, actinomycetes or filamentous fungi.

9. The host cell as claimed in claim 7 wherein the host is any of coliform bacteria, yeast, actinomycetes or filamentous fungi.

10. The host cell as claimed in claim 8 wherein the yeast includes microorganisms that belong to the genus *Saccharomyces*, the genus *Hansenula* or the genus *Pichia*.

11. The host cell as claimed in claim 9 wherein the yeast includes microorganisms that belong to the genus *Saccharomyces*, the genus *Hansenula* or the genus *Pichia*.

12. The host cell as claimed in claim 10 wherein the yeast is *Saccharomyces cerevisiae*.

13. The host cell as claimed in claim 11 wherein the yeast is *Saccharomyces cerevisiae*.

14. The host cell as claimed in claim 8 wherein the filamentous fungi are microorganisms that belong to the genus *Acremonium*, the genus *Humicola*, the genus *Aspergillus*, the genus *Trichoderma* or the genus *Fusarium*.

15. The host cell as claimed in claim 9 wherein the filamentous fungi are microorganisms that belong to the genus *Acremonium*, the genus *Humicola*, the genus *Aspergillus*, the genus *Trichoderma* or the genus *Fusarium*.

16. The host cell as claimed in claim 14 wherein the filamentous fungi are *Acremonium cellulolyticus, Humicola insolens, Aspergillus niger, Aspergillus oryzae, Trichoderma viride*, or *Fusarium oxysporus*.

17. The host cell as claimed in claim 15 wherein the filamentous fungi are *Acremonium cellulolyticus, Humicola insolens, Aspergillus niger, Aspergillus oryzae, Trichoderma viride*, or *Fusarium oxysporus*.

18. A method for producing a β-glucosidase, comprising culturing the host cell of claim 6 followed by collecting the β-glucosidase from the host cell and/or the culture liquid.

19. A method for producing a β-glucosidase, comprising culturing the host cell of claim 7 followed by collecting the β-glucosidase from the host cell and/or the culture liquid.

20. A method for producing a β-glucosidase, comprising culturing the host cell of claim 8, followed by collecting the β-glucosidase from the host cell and/or the culture liquid.

21. A method for producing a β-glucosidase, comprising culturing the host cell of claim 9, followed by collecting the β-glucosidase from the host cell and/or the culture liquid.

22. A method for producing a β-glucosidase, comprising culturing the host cell of claim 10 followed by collecting the β-glucosidase from the host cell and/or the culture liquid.

23. A method for producing a β-glucosidase, comprising culturing the host cell of claim 11 followed by collecting the β-glucosidase from the host cell and/or the culture liquid.

24. A method for producing a β-glucosidase, comprising culturing the host cell of claim 12, followed by collecting the β-glucosidase from the host cell and/or the culture liquid.

25. A method for producing a β-glucosidase, comprising culturing the host cell of claim 13 followed by collecting the β-glucosidase from the host cell and/or the culture liquid.

26. A method for producing a β-glucosidase, comprising culturing the host cell of claim 14 followed by collecting the β-glucosidase from the host cell and/or the culture liquid.

27. A method for producing a β-glucosidase, comprising culturing the host cell of claim 15 followed by collecting the β-glucosidase from the host cell and/or the culture liquid.

28. A method for producing a β-glucosidase, comprising culturing the host cell of claim 16 followed by collecting the β-glucosidase from the host cell and/or the culture liquid.

29. A method for producing a β-glucosidase, comprising culturing the host cell of claim 17 followed by collecting the β-glucosidase from the host cell and/or the culture liquid.

30. The β-glucosidase produced according to the method of claim 18.

31. The β-glucosidase produced according to the method of claim 19.

32. An enzyme composition that comprises the isolated enzyme of claim 1.

33. An enzyme composition that comprises the isolated β-glucosidase of claim 2.

34. An enzyme composition that comprises the β-glucosidase of claim 30.

35. An enzyme composition that comprises the β-glucosidase of claim 31.

36. A feed additive that comprises the isolated enzyme of claim 1.

37. A feed additive that comprises the isolated β-glucosidase of claim 2.

38. A feed additive that comprises the β-glucosidase of claim 30.

39. A feed additive that comprises the β-glucosidase of claim 31.

40. A feed that comprises the isolated enzyme of claim 1.

41. A feed that comprises the isolated β-glucosidase of claim 2.

42. A feed that comprises the β-glucosidase of claim 30.

43. A feed that comprises the β-glucosidase of claim 31.

44. An enzyme agent for silage, which comprises the isolated enzyme of claim 1.

45. An enzyme agent for silage, which comprises the isolated β-glucosidase of claim 2.

46. An enzyme agent for silage, which comprises the β-glucosidase of claim 30.

47. An enzyme agent for silage, which comprises the β-glucosidase of claim 31.

48. Silage, which comprises the isolated enzyme of claim 1.

49. Silage which comprises the isolated β-glucosidase of claim 2.

50. Silage which comprises the β-glucosidase of claim 30.

51. Silage which comprises the β-glucosidase of claim 31.

52. An enzyme agent for food processing, which comprises the isolated enzyme of claim 1.

53. An enzyme agent for food processing, which comprises the isolated 62 -glucosidase of claim 2.

54. An enzyme agent for food processing, which comprises the β-glucosidase of claim 30.

55. An enzyme agent for food processing, which comprises the β-glucosidase of claim 31.

56. Processed food that comprises the enzyme agent of claim 55 for food processing.

57. A processed food, which comprises the enzyme of claim 1.

58. A processed food, which comprises the β-glucosidase of claim 2.

59. A processed food, which comprises the β-glucosidase of claim 30.

60. A processed food, which comprises the β-glucosidase of claim 31.

61. The β-glucosidase of claim 2, which is (a).

62. The β-glucosidase of claim 61 which comprises amino acids 1 to 838 of the amino acid sequence of SEQ ID NO: 2.

63. The β-glucosidase of claim 2 which is (b).

64. The polynucleotide of claim 3 which is (a).

65. The polynucleotide of claim 3 which is (b).

* * * * *

UNITED STATES PATENT AND TRADEMARK OFFICE
CERTIFICATE OF CORRECTION

| | |
|---|---|
| PATENT NO. | : 7,256,031 B2 |
| APPLICATION NO. | : 10/381434 |
| DATED | : August 14, 2007 |
| INVENTOR(S) | : Tomoyuki Fukasawa et al. |

It is certified that error appears in the above-identified patent and that said Letters Patent is hereby corrected as shown below:

<u>Column 21, Line 37</u>
  "gta" should read --gca--;

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,256,031 B2 |
| APPLICATION NO. | : 10/381434 |
| DATED | : August 14, 2007 |
| INVENTOR(S) | : Tomoyuki Fukasawa et al. |

It is certified that error appears in the above-identified patent and that said Letters Patent is hereby corrected as shown below:

Column 1, Line 15
  "polymer of glucose polymer of glucose" should read -- polymer of glucose --.

Column 4, Line 14
  "pectin, methyl-" should read -- pectin methyl- --;

Line 52
  "FERM P-6857" should read -- FERM P-6867 --.

Column 5, Lines 37-39
  " It is also highly active to glycosides with aglycone, such as oligosaccharides and cellobiose." should read --  --.

Column 6, Line 19
  "α-glucosidase" should read -- β-glucosidase --.

Column 7, Line 53
  "those who exist" should read -- those which exist --.

Column 8, Line 67
  "promoter of obh1 gene" should read -- promoter cbh1 gene --.

Column 11, Line 51
  "under seration" should read -- under aeration --.

Column 12, Line 5
  "$CU^{2+}$" should read -- $Cu^{2+}$ --;

Line 14
  "1-glucosidase" should read -- β-glucosidase --.

UNITED STATES PATENT AND TRADEMARK OFFICE
CERTIFICATE OF CORRECTION

PATENT NO.         : 7,256,031 B2
APPLICATION NO.    : 10/381434
DATED              : August 14, 2007
INVENTOR(S)        : Tomoyuki Fukasawa et al.

It is certified that error appears in the above-identified patent and that said Letters Patent is hereby corrected as shown below:

Column 14, Line 39
  "MRP" should read -- MRF' --;

Line 44
  "injected" should read -- infected --;

Line 45
  "phase" should read -- phage --.

Column 15, Line 13
  "QLA" should read -- QIA --.

Column 16, Line 57
  "20 mg" should read -- 20 ng --.

Column 17, Line 18
  "pBGLA-Dr" should read -- pBGLA-Dt. --.

Signed and Sealed this

Eighth Day of January, 2008

JON W. DUDAS
*Director of the United States Patent and Trademark Office*

UNITED STATES PATENT AND TRADEMARK OFFICE
CERTIFICATE OF CORRECTION

PATENT NO. : 7,256,031 B2
APPLICATION NO. : 10/381434
DATED : August 14, 2007
INVENTOR(S) : Tomoyuki Fukasawa et al.

It is certified that error appears in the above-identified patent and that said Letters Patent is hereby corrected as shown below:

In Column 21, Line 38:
"Val" should read --Ala--.

In Column 27, Line 7:
"Val" should read --Ala--.

In Column 34, Line 33 Claim 53:
"62 -glucosidase" should read --β-glucosidase--.

Signed and Sealed this

Twenty-seventh Day of April, 2010

David J. Kappos
*Director of the United States Patent and Trademark Office*

SEQUENCE LISTING

<160> NUMBER OF SEQ ID NOS: 9

<210> SEQ ID NO 1
<211> LENGTH: 2577
<212> TYPE: DNA
<213> ORGANISM: Acremonium cellulolyticus
<220> FEATURE:
<221> NAME/KEY: CDS
<222> LOCATION: (1)..(2574)
<223> OTHER INFORMATION:
<220> FEATURE:
<221> NAME/KEY: sig_peptide
<222> LOCATION: (1)..(60)
<223> OTHER INFORMATION:
<220> FEATURE:
<221> NAME/KEY: mat_peptide
<222> LOCATION: (61)..()
<223> OTHER INFORMATION:

<400> SEQUENCE: 1

```
atg atc aca atg cgg aac agt tta ttg att tcg ctt gcg gca gca        48
Met Ile Thr Met Arg Asn Ser Leu Leu Ile Ser Leu Ala Ala Ala
-20              -15                 -10                  -5 ctt gcc gag ggc aag gca tac tct cct ccc gca tac cct gct ccc tgg    96
Leu Ala Glu Gly Lys Ala Tyr Ser Pro Pro Ala Tyr Pro Ala Pro Trp
           -1   1               5                  10 gcc agc ggc gcc ggg gaa tgg gct caa gct cat caa aga gct gtc gag   144
Ala Ser Gly Ala Gly Glu Trp Ala Gln Ala His Gln Arg Ala Val Glu
             15                  20                  25 ttc gtc tcg caa ttg acc ttg gcc gaa aaa ata aac ttg acg acc ggt   192
Phe Val Ser Gln Leu Thr Leu Ala Glu Lys Ile Asn Leu Thr Thr Gly
         30                  35                  40 gtt ggc tgg gag gga ggg caa tgt gtc ggc aac act gga agc att ccc   240
Val Gly Trp Glu Gly Gly Gln Cys Val Gly Asn Thr Gly Ser Ile Pro
45                  50                  55                  60 cgt ttg ggc ttc cgc agc ctc tgc atg cag gat tca cca ctc ggt gtg   288
Arg Leu Gly Phe Arg Ser Leu Cys Met Gln Asp Ser Pro Leu Gly Val
                 65                  70                  75 aga gac act gat tat aat act gcc ttc cct gct gga gtc aat gtc gcc   336
Arg Asp Thr Asp Tyr Asn Thr Ala Phe Pro Ala Gly Val Asn Val Ala
             80                  85                  90 gct act tgg gat ctc gat ctt gcc tac cgg cgc ggt ata gcc atg gcc   384
Ala Thr Trp Asp Leu Asp Leu Ala Tyr Arg Arg Gly Ile Ala Met Ala
         95                 100                 105 gaa gaa cac cgt ggc aaa ggt gtg gac gtg caa ctt ggt ccc gtt gct   432
Glu Glu His Arg Gly Lys Gly Val Asp Val Gln Leu Gly Pro Val Ala
    110                 115                 120 ggt ccg cta gga aga gta cca gag ggt ggc cgt aac tgg gaa ggt ttc   480
Gly Pro Leu Gly Arg Val Pro Glu Gly Gly Arg Asn Trp Glu Gly Phe
125                 130                 135                 140 gcg ccg gac cct gtg ttg act ggt cag atg atg gca agc act atc caa   528
Ala Pro Asp Pro Val Leu Thr Gly Gln Met Met Ala Ser Thr Ile Gln
                145                 150                 155 ggc atg cag gat acc ggt gtg att gct tgc gca aag cac tat att gga   576
Gly Met Gln Asp Thr Gly Val Ile Ala Cys Ala Lys His Tyr Ile Gly
            160                 165                 170 aac gaa caa gag cac ttc cgt cag ggc tct cag gag aac ttc acc gtt   624
Asn Glu Gln Glu His Phe Arg Gln Gly Ser Gln Glu Asn Phe Thr Val
        175                 180                 185 gct gat gct atc agc tcg aac att gat gac gtt act ttg cac gaa ttg   672
Ala Asp Ala Ile Ser Ser Asn Ile Asp Asp Val Thr Leu His Glu Leu
    190                 195                 200
```

```
                                                       -continued tac ctg tgg ccg ttt gcc gat gcg gtt agg gca ggt gtc ggt tcc gtc        720
Tyr Leu Trp Pro Phe Ala Asp Ala Val Arg Ala Gly Val Gly Ser Val
205                 210                 215                 220 atg tgt tct tac aat caa ata aat aac agc tac tcc tgc ggc aac agc        768
Met Cys Ser Tyr Asn Gln Ile Asn Asn Ser Tyr Ser Cys Gly Asn Ser
                225                 230                 235 tac acc ctg aac cac atc ctc aag ggt gaa ctc gac ttc caa gga ttt        816
Tyr Thr Leu Asn His Ile Leu Lys Gly Glu Leu Asp Phe Gln Gly Phe
            240                 245                 250 gta atg acc gat tgg agt gct caa cac tct ggt gtc ggc gat gct ctt        864
Val Met Thr Asp Trp Ser Ala Gln His Ser Gly Val Gly Asp Ala Leu
        255                 260                 265 gcc gga gct gac atg gat atg cct ggt gat gtg gct ttc gac agt gga        912
Ala Gly Ala Asp Met Asp Met Pro Gly Asp Val Ala Phe Asp Ser Gly
    270                 275                 280 act gct ttc tgg ggt acc aac ttg aca att gcc gtg ctc aat ggc act        960
Thr Ala Phe Trp Gly Thr Asn Leu Thr Ile Ala Val Leu Asn Gly Thr
285                 290                 295                 300 gtt ccc gaa tgg cgt att gac gac atg gct gtt cgt atc atg tct gct       1008
Val Pro Glu Trp Arg Ile Asp Asp Met Ala Val Arg Ile Met Ser Ala
                305                 310                 315 ttc tac aag gtt ggt cgt gat cgt acc cag gtc ccc atc aac ttc gct       1056
Phe Tyr Lys Val Gly Arg Asp Arg Thr Gln Val Pro Ile Asn Phe Ala
            320                 325                 330 agc tgg acc ttg gat acc tat ggc aac gaa tac tac tac gcc ggc gag       1104
Ser Trp Thr Leu Asp Thr Tyr Gly Asn Glu Tyr Tyr Tyr Ala Gly Glu
        335                 340                 345 ggc tac aag gaa atc aac cag cac gtt gat gtg cgt ggt gac cac gcc       1152
Gly Tyr Lys Glu Ile Asn Gln His Val Asp Val Arg Gly Asp His Ala
    350                 355                 360 aaa gtc gtc cgt gaa atc ggc agt gcc agc att gtt ctc ctc aag aac       1200
Lys Val Val Arg Glu Ile Gly Ser Ala Ser Ile Val Leu Leu Lys Asn
365                 370                 375                 380 gtt gat ggt gct ctt cca ttg act ggc tcg gag aag ttt gtc gca gta       1248
Val Asp Gly Ala Leu Pro Leu Thr Gly Ser Glu Lys Phe Val Ala Val
                385                 390                 395 ttt gga gag gac gta ggc tcc aac ccc gat ggt gtc aat ggc tgc tct       1296
Phe Gly Glu Asp Val Gly Ser Asn Pro Asp Gly Val Asn Gly Cys Ser
            400                 405                 410 gac cgt ggc tgt gat aac ggt acc ttg gcc atg gga tgg ggt agt ggt       1344
Asp Arg Gly Cys Asp Asn Gly Thr Leu Ala Met Gly Trp Gly Ser Gly
        415                 420                 425 act gcc aac ttc cct tac ttg gtc acc cct gaa caa gct atc cag gcc       1392
Thr Ala Asn Phe Pro Tyr Leu Val Thr Pro Glu Gln Ala Ile Gln Ala
    430                 435                 440 gaa gtc gtg aag aac ggc ggt atg ttt act gct att acc gac agc ggc       1440
Glu Val Val Lys Asn Gly Gly Met Phe Thr Ala Ile Thr Asp Ser Gly
445                 450                 455                 460 gcc acc gat aca gcc aag acc gtg gct gct caa gct tcg gct tgc cta       1488
Ala Thr Asp Thr Ala Lys Thr Val Ala Ala Gln Ala Ser Ala Cys Leu
                465                 470                 475 gtg ttt gcc aat gca gac tcc gga gaa gga tac atc acc gtt gac ggc       1536
Val Phe Ala Asn Ala Asp Ser Gly Glu Gly Tyr Ile Thr Val Asp Gly
            480                 485                 490 aat gtg gga gat cgt aag aac ttg aca ttg tgg cag aac ggt gaa gct       1584
Asn Val Gly Asp Arg Lys Asn Leu Thr Leu Trp Gln Asn Gly Glu Ala
        495                 500                 505 atg atc tcg gcc gtc gca ggt aac tgc aac aac acc att gtc gtt ctt       1632
Met Ile Ser Ala Val Ala Gly Asn Cys Asn Asn Thr Ile Val Val Leu
```

-continued

```
            510                 515                 520
cat act gtt gga ccc gtt ctt gtc gag gac tgg gtg cac cac cct aac    1680
His Thr Val Gly Pro Val Leu Val Glu Asp Trp Val His His Pro Asn
525                 530                 535                 540 atc act gct gtt ttg tgg gct ggt ctg cct gga gag cag agc ggt aac    1728
Ile Thr Ala Val Leu Trp Ala Gly Leu Pro Gly Glu Gln Ser Gly Asn
                545                 550                 555 tcc ttg gtt gat gtt ctc tac ggc agt gtc aac ccg gga ggc aag act    1776
Ser Leu Val Asp Val Leu Tyr Gly Ser Val Asn Pro Gly Gly Lys Thr
            560                 565                 570 cct ttc acc tgg ggc aag caa cgt tct gat tgg gga gtt gat gtc atc    1824
Pro Phe Thr Trp Gly Lys Gln Arg Ser Asp Trp Gly Val Asp Val Ile
        575                 580                 585 tac gaa ccc aac aat gga gac ggc gct cct cag cag gac ttc act gag    1872
Tyr Glu Pro Asn Asn Gly Asp Gly Ala Pro Gln Gln Asp Phe Thr Glu
    590                 595                 600 ggt atc ttc att gat tac cga cac ttt gac aaa tac aac att acc ccc    1920
Gly Ile Phe Ile Asp Tyr Arg His Phe Asp Lys Tyr Asn Ile Thr Pro
605                 610                 615                 620 acc tac gaa ttc ggt tat ggt ctc agc tac agc acc ttc tca ttc tca    1968
Thr Tyr Glu Phe Gly Tyr Gly Leu Ser Tyr Ser Thr Phe Ser Phe Ser
                625                 630                 635 gac ctc aag gtg act cct atc gct gct tct cct tac cga cca gcc aag    2016
Asp Leu Lys Val Thr Pro Ile Ala Ala Ser Pro Tyr Arg Pro Ala Lys
            640                 645                 650 ggt cag agc ggt ccg gca cct gtg cta ggc aag gtt ttg aac gcc acg    2064
Gly Gln Ser Gly Pro Ala Pro Val Leu Gly Lys Val Leu Asn Ala Thr
        655                 660                 665 gcc tat ctg ttc cct gac tac atc aaa cgc att gaa gcg ttc att tac    2112
Ala Tyr Leu Phe Pro Asp Tyr Ile Lys Arg Ile Glu Ala Phe Ile Tyr
    670                 675                 680 cca tgg ctc aac tcc act gat ctt aag act tcc tct ggt gat cca aac    2160
Pro Trp Leu Asn Ser Thr Asp Leu Lys Thr Ser Ser Gly Asp Pro Asn
685                 690                 695                 700 tac ggc tgg cca act tcc aag tac gtg cct gac ggc gct caa gac ggg    2208
Tyr Gly Trp Pro Thr Ser Lys Tyr Val Pro Asp Gly Ala Gln Asp Gly
                705                 710                 715 tct cca caa cct gtc aac ccc gcc ggt ggt gct cct ggt ggt aac cct    2256
Ser Pro Gln Pro Val Asn Pro Ala Gly Gly Ala Pro Gly Gly Asn Pro
            720                 725                 730 gct ctg tat gac cct gtt gcc gaa gtc act gtc acc gtc aag aac act    2304
Ala Leu Tyr Asp Pro Val Ala Glu Val Thr Val Thr Val Lys Asn Thr
        735                 740                 745 gga aag gtc gct ggt gtc gaa gtg ccc caa ctc tat gtt tcg ctc ggt    2352
Gly Lys Val Ala Gly Val Glu Val Pro Gln Leu Tyr Val Ser Leu Gly
    750                 755                 760 ggt ccc tcc gat gca ccc aag gtt ctt cgt ggc ttt ggc cgt ctt tct    2400
Gly Pro Ser Asp Ala Pro Lys Val Leu Arg Gly Phe Gly Arg Leu Ser
765                 770                 775                 780 ctc ggc gct ggc gag gag act caa tgg act gcc act ttg acc cga cgt    2448
Leu Gly Ala Gly Glu Glu Thr Gln Trp Thr Ala Thr Leu Thr Arg Arg
                785                 790                 795 gac gta tct aac tgg gac act atc aga cag aac tgg gtt gtc aca aac    2496
Asp Val Ser Asn Trp Asp Thr Ile Arg Gln Asn Trp Val Val Thr Asn
            800                 805                 810 tac acc aag act gtt tac gtt ggc aac tct tct cgc aac ttg ccg ctc    2544
Tyr Thr Lys Thr Val Tyr Val Gly Asn Ser Ser Arg Asn Leu Pro Leu
        815                 820                 825 cag cag act ttg gct ctc aac att gga cac taa                        2577
```

Gln Gln Thr Leu Ala Leu Asn Ile Gly His
        830                 835

<210> SEQ ID NO 2
<211> LENGTH: 858
<212> TYPE: PRT
<213> ORGANISM: Acremonium cellulolyticus

<400> SEQUENCE: 2

Met Ile Thr Met Arg Asn Ser Leu Leu Ile Ser Leu Ala Ala Ala
-20                 -15                 -10                 -5

Leu Ala Glu Gly Lys Ala Tyr Ser Pro Pro Ala Tyr Pro Ala Pro Trp
        -1  1               5                   10

Ala Ser Gly Ala Gly Glu Trp Ala Gln Ala His Gln Arg Ala Val Glu
            15                  20                  25

Phe Val Ser Gln Leu Thr Leu Ala Glu Lys Ile Asn Leu Thr Thr Gly
            30                  35                  40

Val Gly Trp Glu Gly Gly Gln Cys Val Gly Asn Thr Gly Ser Ile Pro
45                  50                  55                  60

Arg Leu Gly Phe Arg Ser Leu Cys Met Gln Asp Ser Pro Leu Gly Val
                65                  70                  75

Arg Asp Thr Asp Tyr Asn Thr Ala Phe Pro Ala Gly Val Asn Val Ala
            80                  85                  90

Ala Thr Trp Asp Leu Asp Leu Ala Tyr Arg Arg Gly Ile Ala Met Ala
            95                  100                 105

Glu Glu His Arg Gly Lys Gly Val Asp Val Gln Leu Gly Pro Val Ala
        110                 115                 120

Gly Pro Leu Gly Arg Val Pro Glu Gly Gly Arg Asn Trp Glu Gly Phe
125                 130                 135                 140

Ala Pro Asp Pro Val Leu Thr Gly Gln Met Met Ala Ser Thr Ile Gln
            145                 150                 155

Gly Met Gln Asp Thr Gly Val Ile Ala Cys Ala Lys His Tyr Ile Gly
            160                 165                 170

Asn Glu Gln Glu His Phe Arg Gln Gly Ser Gln Glu Asn Phe Thr Val
        175                 180                 185

Ala Asp Ala Ile Ser Ser Asn Ile Asp Asp Val Thr Leu His Glu Leu
        190                 195                 200

Tyr Leu Trp Pro Phe Ala Asp Ala Val Arg Ala Gly Val Gly Ser Val
205                 210                 215                 220

Met Cys Ser Tyr Asn Gln Ile Asn Asn Ser Tyr Ser Cys Gly Asn Ser
            225                 230                 235

Tyr Thr Leu Asn His Ile Leu Lys Gly Glu Leu Asp Phe Gln Gly Phe
            240                 245                 250

Val Met Thr Asp Trp Ser Ala Gln His Ser Gly Val Gly Asp Ala Leu
            255                 260                 265

Ala Gly Ala Asp Met Asp Met Pro Gly Asp Val Ala Phe Asp Ser Gly
        270                 275                 280

Thr Ala Phe Trp Gly Thr Asn Leu Thr Ile Ala Val Leu Asn Gly Thr
285                 290                 295                 300

Val Pro Glu Trp Arg Ile Asp Asp Met Ala Val Arg Ile Met Ser Ala
                305                 310                 315

Phe Tyr Lys Val Gly Arg Asp Arg Thr Gln Val Pro Ile Asn Phe Ala
            320                 325                 330

Ser Trp Thr Leu Asp Thr Tyr Gly Asn Glu Tyr Tyr Ala Gly Glu
            335                 340                 345

-continued

```
Gly Tyr Lys Glu Ile Asn Gln His Val Asp Val Arg Gly Asp His Ala
    350                 355                 360

Lys Val Val Arg Glu Ile Gly Ser Ala Ser Ile Val Leu Leu Lys Asn
365                 370                 375                 380

Val Asp Gly Ala Leu Pro Leu Thr Gly Ser Glu Lys Phe Val Ala Val
                385                 390                 395

Phe Gly Glu Asp Val Gly Ser Asn Pro Asp Gly Val Asn Gly Cys Ser
            400                 405                 410

Asp Arg Gly Cys Asp Asn Gly Thr Leu Ala Met Gly Trp Gly Ser Gly
        415                 420                 425

Thr Ala Asn Phe Pro Tyr Leu Val Thr Pro Glu Gln Ala Ile Gln Ala
    430                 435                 440

Glu Val Val Lys Asn Gly Gly Met Phe Thr Ala Ile Thr Asp Ser Gly
445                 450                 455                 460

Ala Thr Asp Thr Ala Lys Thr Val Ala Ala Gln Ala Ser Ala Cys Leu
                465                 470                 475

Val Phe Ala Asn Ala Asp Ser Gly Glu Gly Tyr Ile Thr Val Asp Gly
            480                 485                 490

Asn Val Gly Asp Arg Lys Asn Leu Thr Leu Trp Gln Asn Gly Glu Ala
        495                 500                 505

Met Ile Ser Ala Val Ala Gly Asn Cys Asn Asn Thr Ile Val Val Leu
    510                 515                 520

His Thr Val Gly Pro Val Leu Val Glu Asp Trp Val His His Pro Asn
525                 530                 535                 540

Ile Thr Ala Val Leu Trp Ala Gly Leu Pro Gly Gln Ser Gly Asn
                545                 550                 555

Ser Leu Val Asp Val Leu Tyr Gly Ser Val Asn Pro Gly Gly Lys Thr
            560                 565                 570

Pro Phe Thr Trp Gly Lys Gln Arg Ser Asp Trp Gly Val Asp Val Ile
        575                 580                 585

Tyr Glu Pro Asn Asn Gly Asp Gly Ala Pro Gln Gln Asp Phe Thr Glu
    590                 595                 600

Gly Ile Phe Ile Asp Tyr Arg His Phe Asp Lys Tyr Asn Ile Thr Pro
605                 610                 615                 620

Thr Tyr Glu Phe Gly Tyr Gly Leu Ser Tyr Ser Thr Phe Ser Phe Ser
                625                 630                 635

Asp Leu Lys Val Thr Pro Ile Ala Ala Ser Pro Tyr Arg Pro Ala Lys
            640                 645                 650

Gly Gln Ser Gly Pro Ala Pro Val Leu Gly Lys Val Leu Asn Ala Thr
        655                 660                 665

Ala Tyr Leu Phe Pro Asp Tyr Ile Lys Arg Ile Glu Ala Phe Ile Tyr
    670                 675                 680

Pro Trp Leu Asn Ser Thr Asp Leu Lys Thr Ser Ser Gly Asp Pro Asn
685                 690                 695                 700

Tyr Gly Trp Pro Thr Ser Lys Tyr Val Pro Asp Gly Ala Gln Asp Gly
                705                 710                 715

Ser Pro Gln Pro Val Asn Pro Ala Gly Gly Ala Pro Gly Gly Asn Pro
            720                 725                 730

Ala Leu Tyr Asp Pro Val Ala Glu Val Thr Val Thr Val Lys Asn Thr
        735                 740                 745

Gly Lys Val Ala Gly Val Glu Val Pro Gln Leu Tyr Val Ser Leu Gly
    750                 755                 760
```

```
Gly Pro Ser Asp Ala Pro Lys Val Leu Arg Gly Phe Gly Arg Leu Ser
765                 770                 775                 780

Leu Gly Ala Gly Glu Glu Thr Gln Trp Thr Ala Thr Leu Thr Arg Arg
                785                 790                 795

Asp Val Ser Asn Trp Asp Thr Ile Arg Gln Asn Trp Val Val Thr Asn
                800                 805                 810

Tyr Thr Lys Thr Val Tyr Val Gly Asn Ser Ser Arg Asn Leu Pro Leu
            815                 820                 825

Gln Gln Thr Leu Ala Leu Asn Ile Gly His
        830                 835

<210> SEQ ID NO 3
<211> LENGTH: 15
<212> TYPE: PRT
<213> ORGANISM: Acremonium cellulolyticus

<400> SEQUENCE: 3

Lys Ala Tyr Ser Pro Pro Ala Tyr Pro Ala Pro Trp Ala Ser Gly
1               5                   10                  15

<210> SEQ ID NO 4
<211> LENGTH: 14
<212> TYPE: PRT
<213> ORGANISM: Acremonium cellulolyticus

<400> SEQUENCE: 4

Lys Asn Val Asp Gly Ala Leu Pro Leu Thr Gly Ser Glu Lys
1               5                   10

<210> SEQ ID NO 5
<211> LENGTH: 8
<212> TYPE: PRT
<213> ORGANISM: Acremonium cellulolyticus

<400> SEQUENCE: 5

Lys Thr Pro Phe Thr Trp Gly Lys
1               5

<210> SEQ ID NO 6
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t

<400> SEQUENCE: 6
aaraaygtng ayggngc                                                17

<210> SEQ ID NO 7
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
```

```
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t

<400> SEQUENCE: 7 ttncccang traangg                                                17

<210> SEQ ID NO 8
<211> LENGTH: 33
<212> TYPE: DNA
<213> ORGANISM: Artificial Sequence
<220> FEATURE:
<223> OTHER INFORMATION: Synthetic DNA

<400> SEQUENCE: 8
ggggttaaca caatgatcac aatgcggaac agt                             33

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
gggactagtt tagtgtccaa tgttgagagc                                 30
```